United States Patent [19]

Immel et al.

[11] Patent Number: 4,729,977

[45] Date of Patent: Mar. 8, 1988

[54] SUPPORTED CATALYST, PROCESS FOR ITS PREPARATION AND ITS USE FOR THE PREPARATION OF HYDROXYDIPHENYL

[75] Inventors: Otto Immel; Oskar Weissel; Hans-Helmut Schwarz, all of Krefeld, Fed. Rep. of Germany

[73] Assignee: Bayer Aktiengesellschaft, Leverkusen, Fed. Rep. of Germany

[21] Appl. No.: 872,796

[22] Filed: Jun. 11, 1986

[30] Foreign Application Priority Data

Jun. 28, 1985 [DE] Fed. Rep. of Germany ....... 3523205

[51] Int. Cl.[4] .................. B01J 31/04; B01J 31/02; B01J 27/55; B01J 23/26
[52] U.S. Cl. ............................ 502/170; 502/171; 502/174; 502/200; 502/218; 502/221; 502/313; 568/747
[58] Field of Search ............... 502/200, 218, 221, 313, 502/171, 170, 174

[56] References Cited

U.S. PATENT DOCUMENTS

| | | | |
|---|---|---|---|
| 2,588,359 | 3/1952 | Chitwood et al. | 502/218 |
| 3,436,434 | 4/1969 | Lester | 502/313 X |
| 4,057,581 | 11/1977 | Krall et al. | 502/313 X |
| 4,186,145 | 1/1980 | Weissel | 502/313 X |
| 4,288,347 | 9/1981 | Rabinovich et al. | 502/221 X |

FOREIGN PATENT DOCUMENTS

| | | |
|---|---|---|
| 0001425 | 4/1979 | European Pat. Off. |
| 0018763 | 12/1980 | European Pat. Off. |
| 2177951 | 9/1973 | France |

*Primary Examiner*—Patrick P. Garvin, Sr.
*Attorney, Agent, or Firm*—Sprung Horn Kramer & Woods

[57] ABSTRACT

A supported catalyst containing rhodium and compounds of chromium, manganese, alkali metals and, if appropriate, compounds of sulphur is prepared by first applying compounds of chromium and manganese to the catalyst support, subsequently heating the catalyst support thus charged to elevated temperatures and then impregnating it with a rhodium solution, drying it, treating it with an alkali metal solution and, if appropriate, applying sulphur compounds to the catalyst support thus treated. The supported catalyst thus prepared can be used for the dehydrogenation of compounds and/or compound mixtures consisting of completely and/or partly hydrogenated hydroxydiphenyl.

17 Claims, No Drawings

SUPPORTED CATALYST, PROCESS FOR ITS PREPARATION AND ITS USE FOR THE PREPARATION OF HYDROXYDIPHENYL

BACKGROUND OF THE INVENTION

The invention relates to a new supported catalyst and a process for its preparation, and its use for the preparation of hydroxydiphenyl.

A process for the preparation of o-phenylphenol(2-hydroxydiphenyl) by dehydrogenation of cyclohexanone derivatives in the presence of a supported catalyst is known from DE-OS No. (German Published Specification) 2,211,721. The catalyst employed in this process is prepared by depositing a very small amount of palladium, platinum, iridium or rhodium or a mixture of two or more of these elements onto a support, such as silica, aluminium oxide, silica/aluminium oxide or active charcoal, and furthermore adding a suitable amount of an alkali metal. In the Offenlegungsschrift (Published Specification) mentioned, it is found in particular that platinum and palladium have an especially high activity for selective formation of the desired product. The noble metal catalysts employed in this process, however, have too low a selectivity (especially when a rhodium-containing catalyst is used), an inadequate activity or too short a life (in this connection, compare the comparison example).

It is furthermore known from German Patent Specification No. 2,049,809 that hydroxydiphenyl can be prepared by catalytic dehydrogenation of compounds and/or compound mixtures consisting of completely and/or partly hydrogenated hydroxydiphenyl, in the presence of a dehydrogenation catalyst containing nickel, chromium, aluminium, copper and alkali metal. U.S. Pat. No. 4,060,559 likewise describes a process for the preparation of o-phenylphenol by dehydrogenation of cyclohexylphenol, which is carried out in the presence of a supported catalyst containing platinum or palladium. Disadvantages of these processes are likewise the relatively short life of the catalyst and the partly inadequate activity.

SUMMARY OF THE INVENTION

A new supported catalyst has now been found, which is characterized in that it contains rhodium and compounds of chromium, manganese, the alkali metals and, if appropriate, compounds of sulphur.

The customary catalyst supports, in particular α- and γ-aluminium oxide, silica gel, kieselguhr, montmorillonites, pumice and/or active charcoal, preferably γ-aluminium oxide with a high specific surface area ($>50$ m$^2$, preferably 150 to 400 m$^2$/g), are possible as the carrier material.

DETAILED DESCRIPTION OF THE INVENTION

The supported catalyst according to the invention in general has a content of rhodium of about 0.1 to 5% by weight, preferably 0.2 to 2% by weight, a content of chromium and manganese together of about 0.05 to 8% by weight, preferably 0.2 to 5% by weight, a content of alkali metal of about 0.05 to 15% by weight, preferably 0.1 to 10% by weight, and, if appropriate, a sulphur content of about 0.05 to 3% by weight, preferably 0.1 to 1.6% by weight, based on the carrier material.

The weight ratio of the elements chromium and manganese in the supported catalyst according to the invention is about 5:1 to 1:5, preferably 10:9 to 1:2.

The present invention furthermore relates to a process for the preparation of a supported catalyst, which is characterized in that compounds of chromium and manganese are first applied to the catalyst support and the catalyst support thus charged is subsequently heated to elevated temperature and then impregnated with a rhodium solution, dried and treated with an alkali metal solution, and, if appropriate, sulphur compounds are applied to the catalyst support thus treated.

Chromium and manganese are applied to the catalyst support, for example, by conjoint precipitation of a manganese/chromium hydroxide mixture from a chromium salt and manganese salt solution with alkali metal hydroxide solution or ammonia and subsequent washing out of the soluble portions with water. Possible chromium and manganese salts are, in particular, the sulphates, chlorides, acetates and/or nitrates of the elements mentioned. The deposition of the chromium and manganese on the catalyst support can also be effected as ammonium manganese chromate or ammonium alkali metal manganese chromate from a solution of manganese (II) salts and ammonium bichromate by means of ammonia and/or basic alkali metal compounds. Particularly uniform, firmly adhering deposits are obtained if the base is added slowly and uniformly, avoiding relatively large differences in concentration. In a preferred embodiment, the precipitation is therefore carried out by means of urea under hydrolyzing conditions, whereupon the abovementioned conditions are particularly guaranteed.

After application of the chromium and manganese compounds to the catalyst support, the catalyst support thus charged is washed free from sulphate, before it is heated to elevated temperatures (about 200° to 450° C., preferably 250° to 350° C.). Heating of the catalyst support charged with chromium and manganese compounds lasts about 0.5 to 3 hours, preferably 1 to 2 hours.

After heating the catalyst support charged with chromium and manganese, the rhodium is applied by known methods. This can be effected by depositing the rhodium from an aqueous rhodium salt solution, for example a rhodium trichloride, rhodium nitrate or rhodium acetate solution, by precipitation with sodium hydroxide solution. It is also possible first to impregnate the catalyst support charged with a manganese and a chromium compound with a rhodium salt solution and then to treat the catalyst support thus impregnated with sodium hydroxide solution. The two solutions can also be sprayed onto the catalyst support in a heated cooling drum in the same sequence, that is to say first the rhodium salt solution and then the alkali metal solution.

Examples of agents which are suitable for aftertreatment of the rhodium-containing supported catalyst are inorganic and/or organic alkali metal compounds, such as the oxides, hydroxides and/or alcoholates of the alkali metals and the salts of those acids which, either themselves or in the form of their reaction products, are not hydrogenation catalyst poisons in the sense of the customary formulation (for example, according to Zymalkowski: "Katalytische Hydrierung", (1965), page 36; Houben-Weyl, (1955), 4/2, page 257), that is to say, in particular, those which are free from N, P, As, Sb, Se, Te, Cl, Br and I, such as the carbonates, bicarbonates, acetates and/or the salts of other lower carboxylic acids. Examples of alkali metal compounds which may be mentioned are lithium hydroxide, sodium hydroxide, sodium carbonate, sodium bicarbonate, sodium methylate, sodium ethylate, sodium acetate, potassium hydroxide, potassium carbonate, potassium methylate and/or rubidium hydroxide.

The concentration of the alkali metal compounds in the alkali metal solution used is in general about 0.02 to 5N, preferably 0.02 to 2N, in particular 0.01 to 1N.

In a preferred embodiment, sulphur compounds are additionally applied to the rhodium-containing supported catalyst. Examples of suitable sulphur compounds which may be mentioned are the sulphates, sulphites, thiosulphates and thiocyanates of the alkali metals, preferably $K_2SO_4$, $Na_2SO_4$, $Na_2SO_3$, $Na_2S_2O_3$, KSCN and NaSCN. These salts can be employed either individually or as a mixture with one another. However, they can also be dissolved in water, together with the alkali metal compounds, and applied in this way as a mixture to the supported catalyst.

In order to apply the sulphur-containing compounds to the catalyst, the salts mentioned are dissolved in water and the catalyst, which already contains the rhodium and compounds of chromium, manganese and the alkali metals, is impregnated or sprayed with this solution.

The sulphur compounds mentioned are applied to the supported catalyst in an amount such that this has a sulphur content of about 0.05 to 3% by weight, preferably 0.1 to 1.6% by weight, based on the support material.

The catalyst can be dried at temperatures in the range of about 20° to 150° C., preferably 50° to 120° C.

The catalyst according to the invention can be employed directly, after drying, for a dehydrogenation reaction, but it is more advantageous to treat it with hydrogen at 120° to 450° C., preferably at 350° to 420° C., for about 30 to 80 hours, before being used.

The catalyst prepared according to the invention is particularly suitable for the preparation of hydroxydiphenyl by catalytic dehydrogenation of compounds and/or compound mixtures consisting of completely and/or partly hydrogenated hydroxydiphenyl.

The present invention therefore furthermore relates to the use of the catalyst obtained in the manner described above for the preparation of hydroxydiphenyl by catalytic dehydrogenation of compounds and/or compound mixtures consisting of completely and/or partly hydrogenated hydroxydiphenyl.

Suitable starting substances for the use according to the invention of the catalyst for the preparation of hydroxydiphenyl are, for example: 2-cyclohexylidenecyclohexanone, 2-cyclohexenylcyclohexanone, 2-cyclohexylcyclohexanone, 2-cyclohexylcyclohexanol, 2-cyclohexylphenol, 3-cyclohexylphenol, 4-cyclohexylphenol, 2-phenylcyclohexanone and 2-phenylcyclohexanol.

The compounds mentioned are readily accessible. Thus, for example, 2-cyclohexylidenecyclohexanone and 2-cyclohexenylcyclohexanone are obtained by condensation of cyclohexanone in the presence of acid or basic catalysts by known methods. These two compounds are also formed, in addition to 2-cyclohexylcyclohexanone, 2-cyclohexylcyclohexanol and others, as by-products in the catalytic dehydrogenation of cyclohexanol. They can easily be removed from the dehydrogenation mixture by distillation and can be used as a mixture for the 2-hydroxydiphenyl preparation.

Cyclohexylphenol is obtained by known methods by catalytic alkylation of phenol; 2-cyclohexylphenol furthermore also occurs, in addition to 2-phenylcyclohexanone and 2-phenylcyclohexanol, 2-cyclohexylcyclohexanol and 2-cyclohexylcyclohexanone, as a by-product in the 2-hydroxydiphenyl synthesis. The catalytic dehydrogenation of the abovementioned compounds or compound mixtures is in general carried out by passing the compound or compound mixtures in the form of a vapor over the catalyst at temperatures of about 300° to about 400° C., in particular about 320° to about 390° C., under normal pressure or reduced pressure.

The hydroxydiphenyl prepared by the process according to the invention is used, for example, as a preservative for citrus fruits or as a carrier for dyeing with disperse dyestuffs (compare German Patent Specification No. 2,049,809).

EXAMPLE 1

(a) Preparation of the catalyst 100 g of spherical $\gamma$-$Al_2O_3$ (diameter: 2 to 5 mm) with a specific surface area of 350 m$^2$/g were placed in a round-bottomed flask and a solution of 8.3 g of $MnSO_4$·$H_2O$, 6.2 g of $(NH_4)_2Cr_2O_7$ and 45 g of urea in 72 ml of water was added. The flask was kept at 85° C. for one hour, under rotary motion, the liquid which had not been taken up was removed by filtration and the catalyst support was washed free from sulphate and then dried at 110° C. under a waterpump vacuum for 25 hours. The catalyst support thus treated was then heated at 300° C. for 30 minutes. The catalyst support thus charged with chromium and manganese was now uniformly impregnated in a round-bottomed flask with a solution of 2.74 g of rhodium trichloride in 30 ml of water. The moist catalyst pellets were dried at 100° C. under a waterpump vacuum and then impregnated again with a solution of 2.92 g of sodium hydroxide in 30 ml of water. Thereafter, the catalyst pellets were dried at 100° C. under a waterpump vacuum for 43 hours and subsequently heated at 400° C. in a stream of hydrogen of 10 l/hour for 66 hours.

(b) Use of the catalyst 30 ml (25.6 g) of the rhodium-containing supported catalyst were heated to 330° to 350° C. in a vertical, electrically heated glass tube 72 cm in length and 17 mm in internal diameter. 6 g of a mixture of 2-cyclohexenylcyclohexanone and 2-cyclohexylidenecyclohexanone, together with 10 l of hydrogen, were passed per hour into the reaction tube using a calibrated metering device. The liquid starting mixture was vaporized in the upper section of the tube, which contained only packing.

The catalyst was kept at 340° C. during the first 48 hours of operation. A reaction product with the following composition was thereby formed:
2-hydroxydiphenyl: 88%
diphenylene oxide: 5.7%
diphenyl: 3.3%
phenol: 0.4%.

After this starting-up time, the temperature of the catalyst was set at 325° to 330° C. After 1,278; 2,017; 3,179 and 5,770 operating hours, a reaction mixture of the following composition was obtained:

|  | 1,278 hours | 2,017 hours | 3,179 hours | 5,770 hours |
| --- | --- | --- | --- | --- |
| 2-hydroxydiphenyl | 85.2% | 85.1% | 85.4% | 86.6% |

-continued

|  | 1,278 hours | 2,017 hours | 3,179 hours | 5,770 hours |
|---|---|---|---|---|
| 2-cyclohexylphenol | 0.8% | 1.1% | 1.1% | 1.6% |
| diphenylene oxide | 8.7% | 8.6% | 8.7% | 8.1% |
| diphenyl | 3.1% | 3.0% | 2.8% | 2.1% |
| phenol | 0.3% | 0.3% | 0.3% | 0.4% |

EXAMPLE 2

The procedure of Example 1 was repeated, except that only 0.5% by weight of rhodium, based on the support material, was applied to the catalyst and the reaction temperature during the hydrogenation was set at 350° C. 1,191 g of the starting mixture described in Example 1 were employed in the course of 191 hours, and 1,128 g of reaction product were obtained therefrom. The reaction product had the following composition, depending on the length of time the catalyst was used:

|  | 89 hours | 126 hours | 191 hours |
|---|---|---|---|
| 2-hydroxydiphenyl | 84.7% | 84.8% | 84.4% |
| 2-cyclohexylphenol diphenyl | 5.3% | 5.1% | 5.1% |
| diphenylene oxide | 6.1% | 6.5% | 6.8% |
| phenol | 1.2% | 1.1% | 1.0% |

EXAMPLE 3 (Comparison example)

0.5% by weight of rhodium, based on the support material, was applied to 100 g of spherical γ-$Al_2O_3$ (diameter: 2 to 5 mm) with a specific surface area of 350 $m^2$/g, corresponding to DE-OS No. (German Published Specification) 2,211,721, in accordance with Example 1(a), without further addition of the metals mentioned in Example 1. 30 ml (27 g) of this catalyst were employed for dehydrogenation, in accordance with the conditions of Example 2. The reaction product obtained in the course of 60 hours contained less than 5% by weight of the desired 2-hydroxydiphenyl.

This comparison example illustrates that a supported catalyst containing only rhodium is unsuitable for the industrial preparation of 2-hydroxydiphenyl.

EXAMPLE 4

The dehydrogenation reaction was carried out without a carrier gas (that is to say without hydrogen) using 30 ml (24 g) of the catalyst prepared according to Example 1. The temperature in the reaction furnace was thereby initially set at 300° C. and the throughput of the starting mixture (2-cyclohexenylcyclohexanone and 2-cyclohexylidenecyclohexanone) was set at 6.2 g/hour. The temperature of the reaction oven was increased stepwise to 385° C. and the throughput of starting mixture was increased to 26 g/hour in the course of this dehydrogenation experiment. The following table shows the content of 2-hydroxydiphenyl and 2-cyclohexylphenol in the reaction product as a function of the operating hours of the catalyst. The 2-cyclohexylphenol listed in the last column can be re-used in the reaction as starting substance.

| Operating hours | Temperature (°C.) | Throughput in the reaction product (%) | | |
|---|---|---|---|---|
|  |  | g/h | 2-hydroxydiphenyl | 2-cyclohexylphenol |
| 72 | 300 | 6.2 | 60.1 | 23.4 |
| 210 | 330 | 6.2 | 83.6 | 2.5 |
| 362 | 350 | 12.7 | 86.7 | 1.4 |
| 422 | 370 | 26.1 | 85.8 | 4.7 |
| 433 | 380 | 26.5 | 87.1 | 2.4 |
| 527 | 380 | 26.1 | 86.1 | 2.9 |
| 635 | 385 | 25.9 | 86.0 | 3.8 |

EXAMPLE 5

27 g of the catalyst prepared according to Example 1 were additionally impregnated with a solution of 0.81 g of $K_2SO_4$ in 10 ml of water and then dried at 120° C. for 20 hours. 30 ml (25.5 g) of the catalyst thus prepared were heated to 400° C. in a stream of hydrogen (10 l/hour), using the reaction tube described in Example 1, and were kept at this temperature for 68 hours. The oven temperature was then reduced to 350° C. and the dehydrogenation reaction was carried out without a carrier gas. 11.7 g/hour of the isomer mixture 2-cyclohexenylcyclohexanone and 2-cyclohexylidenecyclohexanone were thereby used. 3,972 g of reaction product containing 92.3% of o-phenylphenol and 0.5% of cyclohexylphenol were obtained in the course of 358 hours.

EXAMPLE 6

15 g of the catalyst prepared according to Example 1 were additionally impregnated with a solution of 0.15 g of KSCN in 6 ml of water and then dried at 120° C. for 94 hours. 12.3 g of the catalyst thus obtained were heated to 400° C. in a stream of hydrogen (10 l/hour), and kept at this temperature for 62 hours.

About 6 g of an isomer mixture of 2-cyclohexenylcyclohexanone and 2-cyclohexylidenecyclohexanone were passed over the catalyst thus reduced at 350° to 375° C. 1,387 g of a reaction mixture containing 90% of o-phenylphenol and 2.8% of 2-cyclohexylphenol were thereby obtained in the course of 245 hours.

It will be appreciated that the instant specification and claims are set forth by way of illustration and not limitation, and that various modifications and changes may be made without departing from the spirit and scope of the present invention.

We claim:

1. A supported catalyst comprising rhodium, hydroxides or oxides of chromium and manganese and oxides, hydroxides and/or alcoholates, carbonates, bicarbonates and/or salts of lower carboxylic acids of alkali metals, disposed on a catalyst support, wherein the rhodium is contained in an amount of 0.1 to 5% by weight, the chromium and manganese together are contained in an amount of 0.05 to 8% by weight, and the alkali metal is contained in an amount of 0.05 to 15% by weight, based on the catalyst support weight, and wherein the weight ratio of chromium to magnesium is 5:1 to 1:5.

2. A supported catalyst according to claim 1, further comprising a sulphur compound selected from the group consisting of $K_2SO_4$, $Na_2SO_4$, $Na_2SO_3$, $Na_2S_2O_3$, KSCN and NaSCN, wherein the sulphur content is 0.05 to 3.0% by weight, based on the catalyst support weight.

3. A supported catalyst according to claim 2, wherein the sulphur content is 0.1 to 1.6% by weight, based on the carrier support weight.

4. A supported catalyst according to claim 1, wherein the rhodium is contained in an amount of 0.2 to 2% by weight, the chromium and magnesium together are contained in an amount of 0.2 to 5% by weight, the alkali metal is contained in an amount of 0.1 to 10% by weight, based on the carrier support weight.

5. A supported catalyst according to claim 1, wherein the weight ratio of chromium to magnesium is 10:9 to 1:2.

6. A process for the preparation of a supported catalyst comprising rhodium and compounds of chromium, manganese and alkali metals disposed on a catalyst support, the process comprising depositing chromium and manganese on the catalyst support, heating the support to an elevated temperature, impregnating the support with a rhodium-containing solution, drying and treating the resultant support with an alkali metal-containing solution.

7. A process according to claim 6, wherein the catalyst further contains sulphur and wherein a sulphur compound is applied to the catalyst support after said treating with a solution containing an alkali metal compound.

8. A process according to claim 6, wherein the chromium and manganese are deposited on the catalyst support by conjoint precipitation of a manganese/chromium hydroxide mixture from a chromium salt solution and a manganese salt solution with alkali metal hydroxide solution or ammonia and subsequent washing out of resultant soluable portions with water.

9. A process according to claim 8, wherein said chromium and/or manganese salts are selected from the group consisting of sulphates, chlorides, acetates and nitrates.

10. A process according to claim 6, wherein chromium and manganese are deposited by precipitation ammonium manganese chromate or ammonium alkali metal manganese chromate from a solution of manganese (II) salts and ammonium bichromate by means of ammonia and/or basic alkali metal compounds.

11. A process according to claim 10, wherein the precipitation is carried out by means of urea under hydrolyzing conditions.

12. A process according to claim 6, wherein the elevated temperature is 200° C. to 450° C.

13. A process according to claim 6, wherein the rhodium is deposited from an aqueous rhodium salt solution by precipitation with sodium hydroxide solution.

14. A process according to claim 6, wherein said treating comprises contacting the resultant rhodium-containing supported catalyst with inorganic and/or organic alkali metal compounds, said compounds being free of N, P, As, Sb, Se, Te, Cl, Br and I.

15. A process according to claim 6, wherein the catalyst is further treated with hydrogen at 120° C. to 450° C. for 30 to 80 hours.

16. A supported catalyst according to claim 1, wherein the alkali metal is contained in a compound selected from the group consisting of lithium hydroxide, sodium hydroxide, sodium carbonate, sodium bicarbonate, sodium methylate, sodium ethylate, sodium acetate, potassium hydroxide, potassium carbonate, potassium methylate and rubidium hydroxide.

17. A supported catalyst according to claim 1, wherein the salt of the lower carboxylic acid is an acetate.

* * * * *